United States Patent [19]

Spillert et al.

[11] Patent Number: 4,698,335
[45] Date of Patent: Oct. 6, 1987

[54] PROCESS FOR TREATING A WARM-BLOODED ANIMAL TO BE SUBJECTED TO RADIOTHERAPY

[75] Inventors: Charles R. Spillert, West Orange, N.J.; Corinne Devereux, Bronxville, N.Y.; Eric J. Lazaro, Jersey City, N.J.

[73] Assignee: University of Medicine & Dentistry of New Jersey, Newark, N.J.

[21] Appl. No.: 655,227

[22] Filed: Sep. 27, 1984

[51] Int. Cl.$^4$ ............................................ A61K 31/635
[52] U.S. Cl. ..................................... 514/158; 514/275; 514/917
[58] Field of Search ................. 424/229, 251; 514/158, 514/275, 917

[56] References Cited

U.S. PATENT DOCUMENTS 2,909,522 10/1959 Hitchings et al. ............... 424/251 X

OTHER PUBLICATIONS

Chemical Abstracts, 79:1003742, 1973 (Korn et al.).

Primary Examiner—Leonard Schenkman
Attorney, Agent, or Firm—Weiser & Stapler

[57] ABSTRACT

There is disclosed a process for treating a warm-blooded animal to be subjected to radiotherapy or chemotherapy wherein there is administered to the warm-blooded animal a therapeutically effective amount of a composition selected from the group consisting of 5-methyl-3-sulfanilamidoisoxazole, a salt of 5-methyl-3-sulfanilamidoisoxazole with a pharmaceutically acceptable base, 2,4-diamino-5-(3,4,5-trimethoxybenzyl) pyrimidine, a salt of 2,4-diamino-5-(3,4,5-trimethoxybenzene) pyrimidine with a pharmaceutically acceptable acid and mixtures thereof.

6 Claims, No Drawings

PROCESS FOR TREATING A WARM-BLOODED ANIMAL TO BE SUBJECTED TO RADIOTHERAPY

FIELD OF THE INVENTION

This invention relates to radioprotective compositions, and more particularly to a process for treating a warm-blooded animal with a therapeutically effective amount of a radioprotective composition prior to subjecting the warm-blooded animal to radiotherapy or chemotherapy.

BACKGROUND OF THE INVENTION

In U.S. Pat. No. 2,909,522, there is disclosed 2,4-diamino-5-(3,4,5-trimethoxybenzyl) pyrimidine and a process for preparing same. In U.S. Pat. No. 2,888,455, there is disclosed 5-methyl-3-sulfanilamidoisoxazole and a process for preparing same. In U.S. Pat. No. Re. 28,636 there is disclosed a therapeutically active antibacterial composition comprising 5-methyl-3-sulfanilamidoisoxazole, or a salt thereof together with a pharmaceutically acceptable base and 2,4-diamino-5-(3,4,5-trimethoxybenzyl) pyrimidine or a salt thereof with a pharmaceutically acceptable acid.

SUMMARY OF THE INVENTION

To a warm-blooded animal to be subjected to radiotherapy or chemotherapy, there is administered a therapeutically effective amount of a composition selected from the group consisting of 5-methyl-3-sulfanilamidoisoxazole, a salt of 5-methyl-3-sulfanilamidoisoxazole with a pharmaceutically acceptable base, 2,4-diamino-5-(3,4,5-trimethoxybenzyl) pyrimidine, a salt of 2,4-diamino-5-(3,4,5-trimethoxybenzyl) pyrimidine with a pharmaceutically acceptable acid and mixtures thereof.

DETAILED DESCRIPTION OF THE INVENTION

It has been theorized that radiation induced cellular injury is due to free radical production, and thus tissue damaging effects could be reduced by stabilizing such free radicals. It has been surprisingly found that the resonance stabilized structure of 2,4-diamino-5-(3,4,5-trimethoxybenzyl) pyrimidine and 5-methyl-3-sulfanilamidoisoxazole could stabilze free radicals and hence reduce the tissue damaging effects of free radicals resulting from radiotherapy or the like to a warm-blooded animal.

In a most comprehensive embodiment, the present invention relates to a pharmaceutical composition selected from the group consisting of 5-methyl-3-sulfanilamidoisoxazole, a salt of 5-methyl-3-sulfanilamidoisoxazole with a pharmaceutically acceptable base, 2,4-diamino-5-(3,4,5-trimethoxybenzyl) pyrimidine, a salt of 2,4-diamino-5-(3,4,5-trimethoxybenzyl) pyrimidine with a pharmaceutically acceptable acid and mixtures thereof, useful in the treatment of warm-blooded animals to be subjected to radiotherapy and/or chemotherapy.

In a more particular embodiment, the present invention relates to a pharmaceutical composition, in suitable intravenour or oral dosage forms, which composition is selected from the group consisting of 5-methyl-3-sulfanilamidoisoxazole, a salt of 5-methyl-3-sulfanilamidoisoxazole with a pharmaceutically acceptable base, 2,4-diamino-5-(3,4,5-trimethoxybenzyl) pyrimidine, a salt of 2,4-diamino-5-(3,4,5-trimethoxybenzyl) pyrimidine with a pharmaceutically acceptable acid and mixtures thereof, useful in the treatment of warm-blooded animals to be subjected to radiotherapy and/or chemotherapy.

The expression "salts thereof with pharmaceutically acceptable bases" utilized throughout the present specification to denote salts of 5-methyl-3-sulfanilamidoisoxazole, preferably includes those formed utilizing an alkali metal base, such as sodium hydroxide, potassium hydroxide, etc.

The expression "salts thereof with pharmaceutically acceptable acids" utilized throughout the present specification to denote salts of 2,4-diamino-5-(3,4,5-trimethoxybenzyl) pyrimidine, preferably includes those formed utilizing mineral acids, such as hydrochloric acid, sulfuric acid, etc.; and organic acids, such as acetic acid, citric acid, lactic acid, maleic acid, salicylic acid, etc.

It is also within the scope of this invention to administer each active component individually. Thus, it is possible to formulate each of the components into separate dosage forms in accordance with procedures hereinbefore and hereinafter described for the combination.

The compositions of this invention are prepared simply by admixing 5-methyl-3-sulfanilamidoisoxazole or a salt thereof with a pharmaceutically acceptable base and 2,4-diamino-5-(3,4,5-trimethoxybenzyl) pyrimidine or a salt thereof with pharmaceutically acceptable acid.

In addition to the therapeutically active ingredients mentioned heretofore, the compositions of this invention can contain, as optional ingredients, any of the various adjuvants which are used ordinarily in the production of pharmaceutical preparations. Thus, for example, in formulating the present compositions into the desired intravenous form, one may use, as optional ingredients, antioxidants such as ascorbic acid, anti-platelets such as aspirin, and immunostimulatories such as interferon. It should be fully understood, however, that the optional ingredients herein named or given by way of example only and that the invention is not restricted to the use hereof. On the contrary, other such adjuvants, the identity and use of which are well known in the art, can be, and are, employed in carrying out this invention.

The ratios in which the therapeutically active components are utilized in the compositions of this invention can be varied within wide limits. For example, the compositions can contain from about 1 to about 30 parts of 5-methyl-3-sulfanilamidoisoxazole or an equivalent amount of salt thereof to about 30 to about 1 part of 2,4-diamino-5-(3,4,5-trimethoxybenzyl) pyrimidine or an equivalent amount of salt thereof, preferably from about 5 to about 15 parts of 5-methyl-3-sulfanilamidoisoxazole or an equivalent amount of a salt thereof to one part of 2,4-diamino-5-(3,4,5-trimethoxybenzyl) pyrimidine or an equivalent amount of salt thereof.

The composition of the present invention can be administered in unit dosage forms which contain 500 mg. of 5-methyl-3-sulfanilamidoisoxazole or an equivalent amount of a salt thereof and from about 25 mg. to about 100 mg. of 2,4-diamino-5-(3,4,5-trimethoxybenzyl) pyrimidine or an equivalent amount of a salt thereof. However, it is also within the scope of this invention to utilize a unit dosage form which will contain from about 250 mg. to about 800 mg. of 5-methyl-3- sulfanilamidoisoxazole or an equivalent amount of a salt thereof and from about 12.5 mg. to about 160 mg. of 2,4-diamino-5-(3,4,5-trimethoxybenzyl) pyrimidine or an equivalent amount of a salt thereof. The frequency with which any such unit dosage form will be administered to a warm-blooded animal will vary, depending upon the quantity of medicament present therein and the needs and requirements of the warm-blooded animal. Under ordinary circumstances, however, about a total of 60 mg./kg. of 5-methyl-3-sulfanilamidoisoxazole ang about a total of 8 mg./kg. of 2,4-diamino-5-(3,4,5-trimethoxybenzyl) pyrimidine, in combination, can be administered daily in several doses.

As hereinabove discussed, detailed description is made with reference to unit dosages whether in intravenous or oral form, the frequency and dosage levels are best related with regard to [radioprotective] effectiveness in terms of component levels in the plasma of the warm-blooded animals being treated of the composition selected from the group consisting of 5-methyl-3-sulfanilamidoisoxazole, a salt of 5-methyl-3-sulfanilamidoisoxazole with a pharmaceutically acceptable base, 2,4-diamino-5-(3,4,5-trimethoxybenzyl) pyrimidine, a salt of 2,4-diamino-5-(3,4,5-trimethoxybenzyl) pyrimidine with a pharmaceutically acceptable acid and mixtures thereof. Generally, it is preferably desired to maintain in the plasma of the warm-blooded animal a component level of the 5-methyl-3-sulfanilamidoisoxazole or an equivalent amount of the salt thereof of from about 80 to 160, preferably about 110 $\mu$g./cc. and/or a component level of the 2,4-diamino-5-(3,4,5-trimethoxybenzyl) pyrimidine or an equivalent amount of the salt thereof of from about 5 to 15, preferably 10 $\mu$g./cc.

This invention relates to the invention described in copending applications (Ser. Nos. 655,079; 655,145; 655,080; and 655,144) filed on even date herewith, the teachings of which are incorporated) by reference herein.

The foregoing, notwithstanding, it should be fully understood that the dosages set forth herein are exemplary only and they do not, to any extent, limit the scope or practice of the present invention. As indicated hereinbefore, the combination of this invention has unexpectedly been found to be particularly useful as a radioprotection for warm-blooded animals to be subjected to radiotherapy or chemotherapy.

The invention will be understood better by reference to the following examples which are given for illustration purposes and are not meant to limit the invention.

EXAMPLES

Swiss Webster mice (23±2 gm.) were given intraperitoneally 0.1 cc. saline or 0.1 cc. of I.V. Injectable Composition (Trimethoprim 16 mg./cc., Sulfamethoxazole 80 mg./cc., 320 mg./kgS 64 mg./kgT). One hour later, all animals were given 850 rads from a linear accelerator (8 MeV Photon). No further treatment was given and animals were permitted recovery under normal laboratory conditions. Survival at weekly intervals are set forth in the following Table:

TABLE

| Groups: | Survivals at Weekly Intervals: | | | |
|---|---|---|---|---|
| | 1 Wk. | 2 Wk. | 3 Wk. | 4 Wk. |
| Control (n = 20) | 20 | 16 | 6 | 5 |
| IC (n = 20) | 20 | 20 | 19 | 19 |
| Significance p < (Fisher's Test) | NS | NS | .0001 | .0001 |

30 day survival was the same as the 4 Wk. survival rates. Under the conditions of the experiment, the Injectable Composition is significantly protective against radiation injury.

Numerous modifications and variations of the present invention are possible in light of the above teachings and, therefore, within the scope of the appended claims, the invention may be practiced otherwise than as particularly described.

What is claimed:

1. A process for reducing tissue damage due to radiotherapy in a warm-blooded animal to be subjected to such therapy comprising administering to said warm-blooded animal (a) at least one member selected from the group consisting of 5-methyl-3-sulfanilamidoisoxazole and a salt of 5-methyl-3-sulfanilamidoisoxazole with a pharmaceutically acceptable base, and (b) at least one member selected from the group consisting of 2,4-diamino-5-(3,4,5-trimethoxybenzyl) pyrimidine and a salt of 2,4-diamino-5-(3,4,5-trimethoxybenzyl) pyrimidine with a pharmaceutically acceptable acid, said (a) and (b) being administered in an amount effective to reduce tissue damage.

2. The process as defined in claim 1 wherein said therapeutically effective amount of the composition comprises from about 250 mg. to about 800 mg. of 5-methyl-3-sulfanilamidoisoxazole or an alkali metal salt thereof with a pharmaceutically acceptable base and from about 12.5 mg. to 160 mg. of 2,4-diamino-5-(3,4,5-trimethoxybenzyl) pyrimidine or a salt thereof with a pharmaceutically acceptable acid.

3. The process as defined in claim 1 wherein a component level in the plasma of the warm-blooded animal of said 5-methyl-3-sulfanilamidoisoxazole or an alkali metal salt thereof with a pharmaceutically acceptable base is maintained at from about 80 to 160 $\mu$g./cc.

4. The process as defined in claim 3 wherein said component level is preferably about 110 $\mu$g./cc.

5. The process as defined in claim 1 wherein a component level in the plasma of the warm-blooded animal of said 2,4-diamino-5-(3,4,5-trimethoxybenzyl) pyrimidine or a salt thereof with a pharmaceutically acceptable acid is maintained at from about 5 to 15 $\mu$g./cc.

6. The process as defined in claim 5 wherein said component level is preferably about 10 $\mu$g./cc.

* * * * *